(12) United States Patent
Mantovani et al.

(10) Patent No.: US 11,942,225 B2
(45) Date of Patent: Mar. 26, 2024

(54) SYSTEM AND METHOD FOR IDENTIFYING ALTERATIONS IN A MUSCLE-SKELETON SYSTEM OF A SPECIFIC SUBJECT

(71) Applicant: Alyve Medical, Inc., Denver, CO (US)

(72) Inventors: Matteo Mantovani, Reggio Emilia (IT); Pietro Garofalo, Forli' (IT)

(73) Assignee: ALYVE MEDICAL, INC., Denver, CO (US)

( * ) Notice: Subject to any disclaimer, the term of this patent is extended or adjusted under 35 U.S.C. 154(b) by 209 days.

(21) Appl. No.: 15/540,887

(22) PCT Filed: Dec. 28, 2015

(86) PCT No.: PCT/IB2015/060000
§ 371 (c)(1),
(2) Date: Jun. 29, 2017

(87) PCT Pub. No.: WO2016/108168
PCT Pub. Date: Jul. 7, 2016

(65) Prior Publication Data
US 2018/0011986 A1 Jan. 11, 2018

(30) Foreign Application Priority Data
Dec. 29, 2014 (IT) .............................. I2014A002266

(51) Int. Cl.
G16H 50/50 (2018.01)
A61B 5/00 (2006.01)
(Continued)

(52) U.S. Cl.
CPC ............ *G16H 50/50* (2018.01); *A61B 5/1114* (2013.01); *A61B 5/45* (2013.01); *G16Z 99/00* (2019.02)

(58) Field of Classification Search
CPC ........ G16H 50/20; G16H 50/30; G16H 50/50; G16H 50/70; G06F 19/00; A61B 5/11–1178; A61B 5/45–4595
See application file for complete search history.

(56) References Cited

U.S. PATENT DOCUMENTS

| 8,862,202 B2 | 10/2014 | Alexander et al. |
| 2006/0022833 A1* | 2/2006 | Ferguson ............... A63F 13/212 340/573.1 |

(Continued)

FOREIGN PATENT DOCUMENTS

WO 2010/099361 9/2010

OTHER PUBLICATIONS

PCT/IB2015/060000, dated May 30, 2015, International Search Report.

*Primary Examiner* — Benjamin S Melhus
*Assistant Examiner* — Samuel C Kim
(74) *Attorney, Agent, or Firm* — Matthew M. Hulihan; Heslin Rothenberg Farley & Mesiti PC

(57) ABSTRACT

Systems and methods for identifying alterations in a musculoskeletal system of a subject are disclosed. After detecting physical quantities representative of a state of the subject, a biomechanical model for the subject is identified and combined movements of muscles and bones as a function of said physical quantities and of said biomechanical model are determined. The combined movements are converted into a plurality of movement steps of segments and joints. Parameters representative of the alterations are computed, and the parameters are compared with predefined reference values representative of alteration thresholds in the musculoskeletal system. The alterations are identified as a function of a failed matching between the computed parameters and the predefined reference values, and the belonging (Continued)

of this correspondence to one or more groups of musculo-skeletal pathologies as a function of said identified alteration is determined.

14 Claims, 3 Drawing Sheets

(51) Int. Cl.
*A61B 5/11* (2006.01)
*G16Z 99/00* (2019.01)

(56) References Cited

U.S. PATENT DOCUMENTS

| | | | |
|---|---|---|---|
| 2008/0181470 A1* | 7/2008 | Camus | A61B 6/505 |
| | | | 382/128 |
| 2009/0322763 A1* | 12/2009 | Bang | G06F 3/011 |
| | | | 345/474 |
| 2010/0191088 A1* | 7/2010 | Anderson | A61B 17/7074 |
| | | | 600/373 |
| 2012/0310075 A1* | 12/2012 | Russell | A61B 5/1071 |
| | | | 600/407 |
| 2013/0226039 A1* | 8/2013 | Shani | G16H 40/40 |
| | | | 600/595 |
| 2016/0086500 A1* | 3/2016 | Kaleal, III | A61B 5/43 |
| | | | 434/257 |

\* cited by examiner

Fig.2a
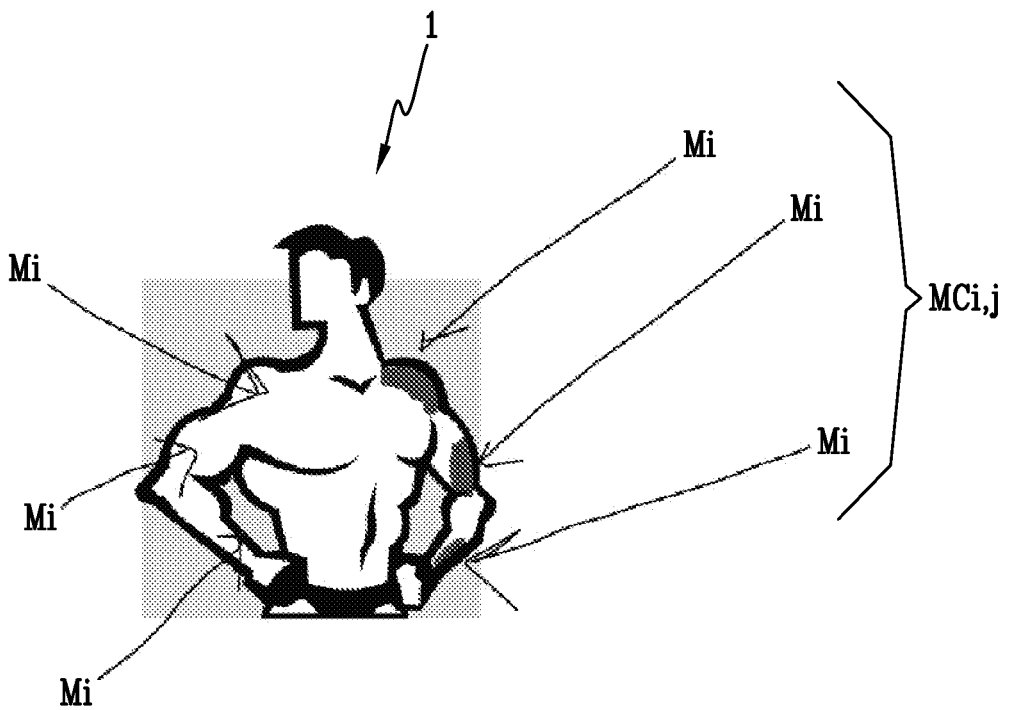
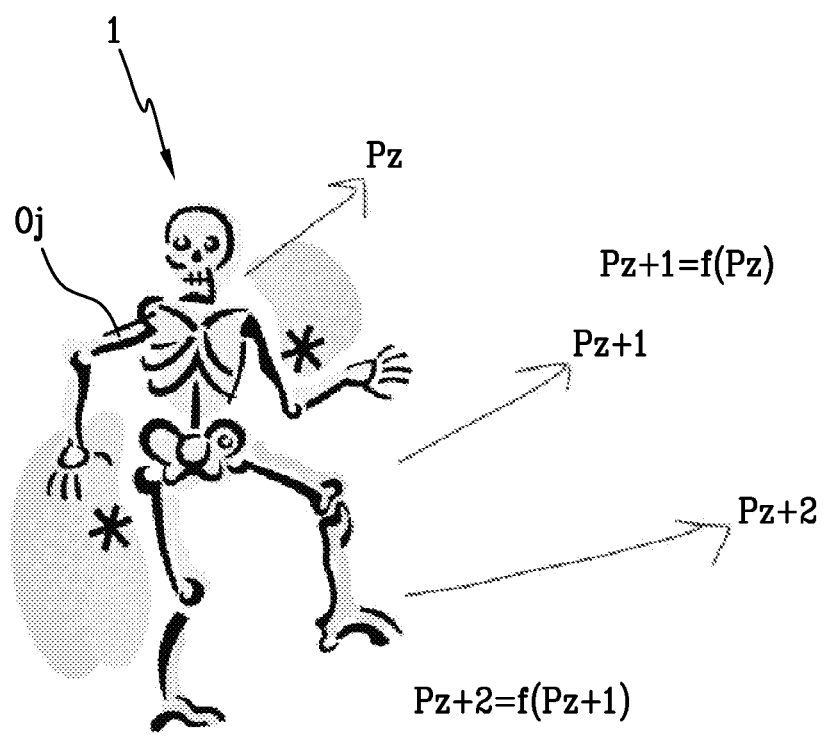
$Pz+1=f(Pz)$
$Pz+2=f(Pz+1)$
Fig.2b

SYSTEM AND METHOD FOR IDENTIFYING ALTERATIONS IN A MUSCLE-SKELETON SYSTEM OF A SPECIFIC SUBJECT

FIELD OF APPLICATION

The present invention relates to a method and a system for processing data representative of a state of a specific subject.

In particular, the present invention relates to a method and a system for processing physical quantities representative of a state of a subject.

More in particular, the invention relates to a method for identifying alterations in the musculoskeletal system of a subject.

The following description is given with reference to physical quantities measured in a clinical setting and in sports medicine, solely for the purpose of simplifying the disclosure thereof.

PRIOR ART

Automated systems for detecting the movement of a human body are available in the market; these include electromechanical systems, systems based on camera recordings, wireless systems applied to the human body and rehabilitation systems based on video games.

All these systems aim to provide information regarding the kinematics of the movement of a human body by combining sensor data originating from specific hardware and data originating from software processing.

By generating a biomechanical model that describes the kinematics of the human body, such systems provide the user with graphic information relating to segments and joints of the human body.

A first group of such systems enables a user to generate reporting data which include kinetic and kinematic information based on the movement of the human body being monitored.

However, the parameters processed by known software programs are typically difficult to interpret for user who is not expert with the instruments/technique and/or the method/measurement algorithm.

This is mainly due to the fact that the instruments and techniques or integration thereof are presently used in clinical settings or in sports medicine and provide a large set of data regarding the movement of multiple body segments/joints without there being any possibility of applying an optimised selection of this data.

The competences of the end user of such instruments aimed at monitoring the human body or diagnosing an alteration are generally far from being technical or technological. The interpretation of the data becomes even more complex when a number of detection sensors are used (for example motion sensors and sensors of muscular activity), exponentially increasing the list of data that must be interpreted by the end user; this concretely prevents the identification of alterations that occur in the musculoskeletal system, rather than facilitating their identification.

In other words, with systems for generating reporting data, the end user has concrete difficulties in using the products of the prior art due to the excessive complexity of the information generated.

A second group of systems is represented by rehabilitation systems aimed at providing direct visual feedback to the subject/patient by means of a virtual environment/videogame which provides simple scores according to the number of objects gathered or moved or the number of times a certain body segment is moved in a certain direction. However, these scores are not directly linked to the manner in which the movement was made and are thus not significant from the standpoint of the functionality achieved.

At the same time, the movement of a primary joint relative to the movement of a secondary joint is not analysed by known processing software. In addition, the above-mentioned visual feedback requires an optimisation of the data in order to become realistic in representing the body. However, with these systems, the end user has imprecise, incomplete information that is scarcely meaningful.

It is well known that the movement of the human body takes place according to specific models controlled by the central nervous system and learning mechanisms that work in such a way that during a specific step of a movement a certain muscle acts, whether in synergy or not with a secondary muscle, in such a way as to rotate a joint by a certain number of degrees.

Disadvantageously, the current evaluations performed by prior art systems on the upper body do not take into consideration the movement of segmentation during the main steps thereof (forward and backward during the raising of an arm, for example), in which a synergy occurs among multiple segments and joints.

This, disadvantageously, implies that there can be no interpretation of a specific movement step, when the parameters are calculated.

In general, the lack of methods for automatically interpreting the kinematic or kinetic data limits the ability of the prior art systems shown (and not) to identify alterations, apply specific rehabilitation programs and plan sports or workplace injury prevention programs.

The variability in the characteristics of a human body from one person to another is recognised as a limiting factor when interpreting movement detection data for clinical purposes; in fact, the methods implemented in prior art systems and products to describe the human body from a biomechanical viewpoint are generally based on a basic statistical analysis, where intra- and inter-subject variability are not taken into consideration when standard reference data are used.

The variability due to the measurement model or biomechanical protocol used to describe the human body is also a limiting factor when degrees of alteration due to a certain pathology are of the same order of magnitude as alterations due to imprecision in the protocol/biomechanical model (Kontaxis et al.).

Once again, therefore, there is an evident inability of the prior art systems/products to identify alterations, apply specific rehabilitation programs and plan sports and workplace injury prevention programs.

Document U.S. 2010/0191088 discloses methods and systems for carrying out a surgical procedure using implantable sensors. The methods include providing one or more implantable sensors, where every sensor is configured to be implanted in anatomic parts of a subject.

The methods/systems described are invasive.

The object of the present invention is to provide an efficient method/system for identifying alterations in the musculoskeletal system of a specific subject.

A particular object of the present invention is to provide a method/system for identifying of alterations in the musculoskeletal system of a specific subject that ensures a precise identification of the alteration.

Another specific object of the present invention is to provide a method/system for identifying of alterations in the musculoskeletal system of a subject that is also easy for non-specialised personnel to understand and use.

A further object of the present invention is to provide a method/system for identifying of alterations in the musculoskeletal system of a subject that does not entail any physical suffering for the subject.

SUMMARY OF THE INVENTION

In a first aspect of the invention, these and other objects are achieved by a method for identifying alterations in a musculoskeletal system of a subject, wherein the method comprises the steps of:

associating, with the subject, detecting means capable of detecting physical quantities representative of a state of the subject;

detecting said physical quantities through said detecting means;

identifying a biomechanical model for said subject;

determining combined movements of muscles and bones as a function of said detected physical quantities and the identified biomechanical model;

converting said combined movements into a plurality of movement steps of segments and joints;

computing parameters representative of said alterations as a function of either or both:
said movement steps;
said biomechanical model;

comparing said computed parameters and predefined reference values representative of alteration thresholds in said musculoskeletal system;

identifying said alterations as a function of a failed matching between said computed parameters and said predefined reference values.

determining the belonging of an alteration to one or more groups of musculoskeletal pathologies as a function of said identified alteration.

Preferably, the method comprises a step of displaying said identified alterations in real time.

Preferably, the step of determining said combined movements of muscles and bones comprises the step of displaying said muscles and bones in a combined view, preferably in a three-dimensional representation.

Preferably, in said step of converting said combined movements into a plurality of movement steps of segments and joints, said movement steps are calculated as a function of:
first joint parameters of a first joint and
at least a second joint parameter computed as a function of second joints affected by the movement of the first joint
and said step of computing said parameters representative of said alterations is further carried out as a function of said joint parameters.

Preferably, in said converting step, said second joints move relative to said first joint in a condition between:
movement in synergy with said first joint;
movement in compensation for the movement produced by said first joint.

Preferably, said converting step takes place by transformation of the joint degrees expressed in the system of coordinates integral with the joint into degrees of movement of the bone distal to the joint, around respective axes belonging to the system of coordinates integral with the skeleton.

Preferably, said step of identifying said biomechanical model for said subject comprises the steps of:

asking the user for specific measurements in order to calibrate the system as a function of one or more among a scenario, environment and number of detecting means applied to the subject;

asking the user to carry out a specific procedure of anatomic positioning, based on a biomechanical description of human body segments and joints, by means of a validated measuring protocol Preferably, said step of associating said detecting means with said subject comprises one or more among the steps of:
positioning said detecting means on said subject;
applying said detecting means to said subject.

Preferably, said joint parameters are numerical parameters.

Preferably, in said step of comparing said computed parameters and predefined reference values, the values of the comparison are represented as "clinical scores".

Preferably, each "clinical score" is computed as a function of the joint parameters of one or more joints affected by the movement or as a function of another clinical score.

Preferably, the method comprises, following said step of determining said combined movements, a step of memorising said combined movements and displaying said muscles and bones in a combined view, preferably in a three-dimensional representation.

Preferably, said step of detecting said physical quantities through said detecting means is carried out real time.

Preferably, the method further comprises providing an instruction procedure for guiding the user in the various steps.

Preferably, said user instruction procedure comprises the steps of:

providing a graphic interface configured to carry out one or more among the steps of:
controlling the detection of physical quantities;
changing the display method;
showing how to position the detecting means;
showing how to activate the detecting means;
showing the subject how to position him/herself for a correct analysis;
showing data configuration/integration questions to the subject;
generating said biomechanical model as a function of the execution of one or more of the preceding steps.

Preferably, said detecting means comprise one or more among:
sensors; probes; or the like.

In a second aspect of the invention, the above-mentioned objects and other objects are achieved by a system for identifying alterations in a musculoskeletal system of a subject, wherein the system comprises:

detecting means, associated with said subject, and capable of detecting physical quantities representative of a state of said subject;

a detecting unit configured to detect said physical quantities through said detecting means;

an identifying unit configured to identify a biomechanical model for said subject;

a determining unit configured to determine combined movements of muscles and bones as a function of said physical quantities detected and of said identified biomechanical model;

a conversion unit configured to convert said combined movements into a plurality of movement steps of segments and joints;

a processing unit for processing alteration data comprising:

a computing module configured to compute parameters representative of said alterations as a function of one or more among:

said movement steps;
said joint parameters;
said biomechanical model;
a comparison module configured to compare:
said computed parameters and
predefined reference values representative of alteration thresholds in said musculoskeletal system;
an identification module configured to identify said alterations as a function of a failed matching between said computed parameters and said predefined reference values.
a classification module configured to determine the belonging of an alteration to one or more groups of musculoskeletal pathologies as a function of said alterations identified by said identification module.

Preferably, the system comprises a comparison module configured to generate comparative values represented as "clinical scores".

Preferably, each "clinical score" is computed as a function of the joint parameters of one or more joints affected by the movement or as a function of another clinical score.

Preferably, the system further comprises a display unit configured to display said identified alterations.

Preferably, said determining unit comprises a display module configured to display said muscles and bones in a combined view, preferably three-dimensional.

Preferably, the system further comprises a memory unit for memorising said combined movements and said combined view of said muscles and bones.

Preferably, the conversion unit is configured to convert said combined movements into a plurality of movement steps of segments and joints, wherein said movement steps are calculated as a function of:

first joint parameters of a first joint and
at least a second joint parameter computed as a function of second joints affected by the movement of the first joint.

Preferably, said identifying unit further comprises:

a first request module 22 configured to ask the user for specific measurements in order to calibrate the system as a function of one or more among scenario, environment, and number of detecting means applied to the subject;
a second request module 23 configured to ask the user to carry out a specific procedure of anatomic positioning based on a biomechanical description of human body segments and joints.

Summing up, the method/system of the present invention achieves at least the following technical effects:

it is efficient, since it detects alterations in the musculoskeletal system of a specific subject;
it is precise in identifying the alteration;
it is also easy for non-specialised personnel to understand and use;
it does not cause physical suffering to the subject since it is non-invasive.

The technical effects/advantages mentioned and other technical effects/advantages will emerge in more detail from the description, given below, of an example embodiment illustrated by way of non-limiting example with reference to the attached drawings.

BRIEF DESCRIPTION OF THE DRAWINGS

FIGS. 2a and 2b and 3 are detailed views of blocks of FIG. 1.

DETAILED DESCRIPTION

Figure 1:
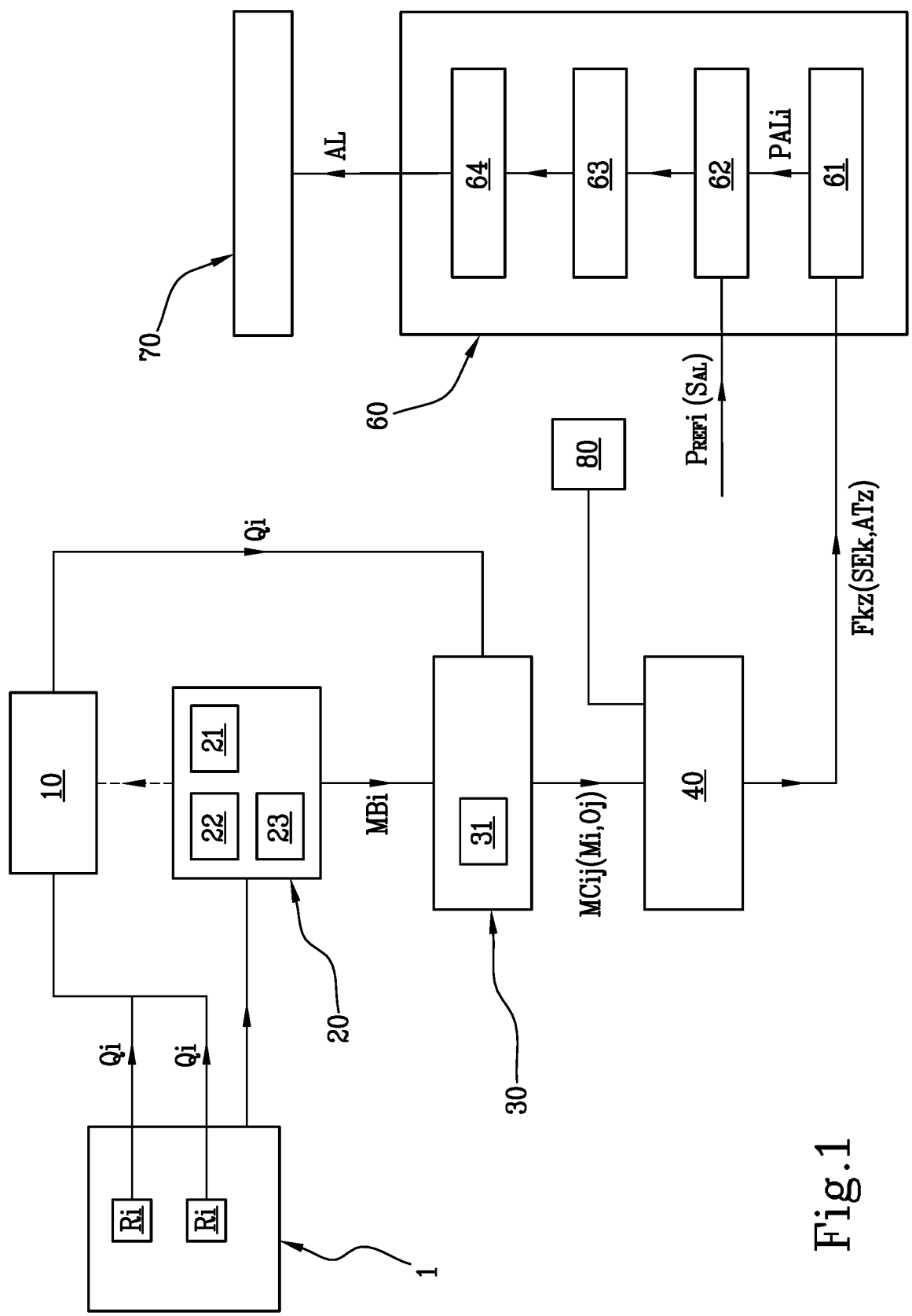
FIG. 1 is a block diagram of the system of the invention which shows components capable of implementing the method of the invention.

With particular reference to the drawings, FIG. 1 shows a system for identifying alterations in the musculoskeletal system of a subject, wherein the system comprises detecting means Ri associated with the subject 1 and capable of detecting physical quantities Qi representative of a state St of the subject 1, a detecting unit 10 configured to detect the physical quantities Qi through the detecting means Ri, an identifying unit 20 configured to identify a biomechanical model MBi for said subject 1, a determining unit 30 configured to determine combined movements MCij of muscles Mi and bones Oj as a function of the detected physical quantities Qi and of the identified biomechanical model MBi, a display unit 31 configured to display the combined movements MCij of muscles Mi and bones Oj in an overall combined view, a conversion unit 40 configured to convert the combined movements MCij into a plurality of movement steps Fkz of segments SEk and joints ATz, a processing unit 60 comprising a computing module 61 configured to compute parameters PALi representative of the alterations AL, a comparison module 62 configured to compare the computed parameters PALi with predefined reference values $P_{REF}i$, an identification module 63 configured to identify the alterations AL as a function of a failed matching between the computed parameters PALi and the predefined reference values $P_{REF}i$, and a classification module 64 configured to determine the belonging of the identified alteration AL to one or more groups of musculoskeletal pathologies as a function of the identified alteration AL.

In a first preferred embodiment, the invention is applied to the musculoskeletal movements of a baseball pitcher.

Detecting means Ri capable of detecting physical quantities Qi representative of a state St of the subject are associated with the pitcher.

In particular, said detecting means Ri are associated with the subject 1 by positioning the same on said subject 1 and/or applying them to said subject 1.

Preferably, the detecting means Ri comprise platforms based on sensors R1, preferably time synchronised with one another through a Wi-Fi or Bluetooth connection.

Preferably, the platforms are applied to the body of the subject using dedicated pull-off straps or adhesive material for the skin or tissues, fitted with sensors, which incorporate the platforms for detecting the physical quantities Qi representative of a state St of the subject.

Alternatively or in addition, the detecting means Ri comprise electromyographic probes R2 which measure, preferably by detecting electrical activity, muscle contractions monitored by pairs of electrodes positioned on the surface of the muscle and connected to the probes R2.

A detecting unit 10 is configured to detect the physical quantities Qi through the detecting means Ri.

The detecting unit 10 operates in real time and collects the information, i.e. the physical quantities Qi coming from the aforesaid detecting means Ri or similar ones, aligning them in time, and sends this information to a low-level graphic user interface, in particular an identifying unit 20.

The identifying unit 20 is configured to identify a biomechanical model MBi for the subject 1.

The invention comprises a user instruction procedure which guides the user in all steps of the method of the invention.

In other words, the invention comprises a specific "wizard" which helps the user to identify and make decisions concerning strategies, make corrections, communicate with the subject undergoing examination or with another operator and generate digital reports.

The technical effect achieved is to make the process of the invention also easy for non-specialised personnel to understand and use.

The user instruction procedure comprises a graphic interface 21 configured to perform one or more among the steps of:
controlling the detection of the physical quantities Qi;
changing the display method;
showing how to position the detecting means Ri;
showing how to activate the detecting means Ri;
showing the subject 1 how to position himself for a correct analysis;
showing data configuration/integration to the end user.

The generation of the biomechanical model MBi of the subject 1 takes place as a function of the execution of one or more of the preceding steps.

The technical effect achieved is a generation of a virtual representation of clinical information for a user who is not expert with the measurement protocol, the processing algorithms and the technology applied.

In other words, the graphic interface 21 is provided with buttons and controls that guide the user through a step-by-step procedure controlled by the identifying unit 20.

A first screen shows the procedure for activating the detecting means Ri, the connection with the detecting means Ri and the selection of the type of movement that the subject 1 will be asked to perform, whether or not there is a need to keep track of the information of more than one detecting means Ri, and the type of display required.

The connection with the detecting means is automatically activated and maintained until the user decides to stop the analysis by means of a dedicated pushbutton.

In a second screen it is explained to the user how to position the detection means Ri already connected on the body of the subject 1. Preferably, the instructions are provided in the form of a video integrated in the screen.

In a third screen the identifying unit 20 activates the detecting means via the detecting unit 10 and asks the user to wait for a predefined time, for example 10 seconds, before going on to the next step in order to enable the detecting unit 10 to stabilise the output transients.

The third screen also shows the movements the subject is allowed to make in this period and a subsequent request to the same subject 1 to maintain a stationary posture or perform specific dynamic movements for a reliable detection based on validated measurement protocols.

Preferably, the instructions are provided in the form of a video integrated in the screen, as in the preceding step.

At the end of this step, the identifying unit 20 generates a biomechanical description MBi of the human body segments involved in the analysis with the identified detecting means.

The technical effect achieved is the maintaining of a constant ratio between the detecting means Ri and anatomical body segments such as the torso, scapula and humerus, of the analysed part of the subject.

In still other words, and in summary, the identification of the biomechanical model MBi for the subject 1 comprises the steps of:

asking the user for specific measurements (Mi) in order to calibrate the system as a function of scenario, environment and/or number of detecting means Ri applied to the subject 1;
asking the user to carry out a specific procedure of anatomic positioning based on the biomechanical description of human body segments and joints.

The technical effect achieved is a specific, optimised multi-segment and multi-joint analysis on the subject which ensures a limitation of the variability among subsequent analyses of the same subject or similar analyses of different subjects due to errors both in the biomechanical model and in hardware components.

Furthermore, the reliability of the data generated and in general of the system as a whole is improved.

At the end of the analysis, the identifying unit 20 provides feedback to the user to confirm the successful conclusion of the generation of the biomechanical description MBi of the human body segments involved in the analysis. If this generation is not successfully concluded, the identifying unit 20 invites the user to repeat the preceding steps again.

The invention comprises a determining unit 30.

The determining unit 30 is configured to determine combined movements MCij of muscles Mi and bones Oj as a function of the detected physical quantities Qi and of the identified biomechanical model MBi.

Muscles Mi and bones Oj are shown respectively in FIGS. 2a and 2b.

In a fourth screen, the determining unit 30 uses the biomechanical model MBi of the preceding step and combines it with a method for extracting joint rotation angles in order to compute the joint kinematics in real time for each data sample.

In particular, joint angles include 3D rotation angles of humerothoracic, glenohumeral and scapulothoracic joints.

For each data sample, these values expressed in degrees are transferred to the display method previously selected by the user in order to monitor the virtual joints in the 3D environment.

A specific part of the determining unit 30 checks the manner in which the values are converted so as to generate the 3D movement, i.e. the combined movement MCij.

With reference to FIG. 2b, the combined movement 3D is displayed in the form of a human skeleton, including the torso, head, scapula, humerus, forearm and hand for both the left and right limbs represented by bones in a virtual 3D environment.

A display module 31 of the determining unit 30 is configured to display the muscles Mi and the bones Oj in a combined view, preferably three-dimensional.

The conversion takes place by transforming the joint degrees expressed in the system of coordinates integral with the joint into degrees of movement of the bone distal to the joint around respective axes belonging to the system of coordinates integral with the skeleton. The conversion is performed in such a way that the ratio between the value in degrees used and the corresponding degrees of bone movement is 1:1 at every instant of measurement.

The virtual environment can comprise overlaying virtual avatars on the skeleton, of male or female sex and different sizes or statures, based on the characteristics of the subject 1. The avatars integrally follow the movements of the skeleton on the basis of a direct conversion between avatar and skeleton.

For each pair of bones in the skeleton in FIG. 2b, tendons and superficial muscles of the upper limb are represented in FIG. 2a using textures which represent muscles of the upper human limbs.

The lengths of tendons and colour of the textures are dynamically controlled based on the value of the electrical signal (mV) coming from the probes EMG on a real-time basis. A set of thresholds is selected by the user in a configuration section of the software. These thresholds (μV) are used to modulate the colour of the textures for each muscle based on the value of the signal for each muscle.

The technical effect achieved is to enable a rapid, simplified understanding of muscle activity in correlation with movement.

A series of reproduction and recording controls are identified by standard pushbuttons that enable the display to be started, interrupted and recorded.

The invention comprises a conversion unit 40 (FIG. 1) configured to convert said combined movements (MCij) into a plurality of movement steps (Fkz) of segments (SEk) and joints (ATz).

In other words, the conversion unit 40 carries out a segmentation of the previously recorded process, identifying the steps of the movement.

In other words, movement steps Fkz are calculated as a function of:
first joint parameters (Pz) of a first joint (ATz) and at least a second joint parameter (Pz+1) computed as a function of second joints (ATz+1) affected by the movement of the first joint (ATz).

The technical effect achieved by the segmentation of the movement into its main steps is to enable alterations in the musculoskeletal system to be identified based on the behaviour of a plurality of body parts during movement; this contributes to an understanding of the correct rehabilitation program for the specific segment/joint/muscle.

The movement steps identified are displayed in a second part of the fourth screen which comprises dedicated panels showing a Cartesian plane XY that is updated point by point using the angular values computed for each data sample.

By means of a specific control pushbutton the user can choose whether or not to render a specific background of the Cartesian plane visible in such a way as to show previously recorded values of the same type used for the real-time display.

The type of data displayed in the Cartesian plane is selected according to the subject undergoing examination.

Since the subject is a baseball athlete and his pitching performance is under examination, the X axis shows the abduction rotation of his humerus (values in degrees) and the Y axis shows the axial rotation of the scapula (values in degrees).

When the user presses the stop pushbutton, that is, interrupts the simulation, a memory unit 80 (FIG. 1) memorises the virtual 3D movement and graphic session in a file, preferably proprietary.

The invention comprises a processing unit 60 for processing alteration data.

The processing unit 60 comprises a computing module 61 configured to compute parameters PALi representative of the alterations AL as a function of one or more among:
the movement steps Fkz;
the joint parameters (Pz;Pz+1);
the biomechanical model (MBi);

The technical effect achieved is the obtainment of numbers that are easy to interpret, memorise, compare and share.

In other words, a fifth screen displays the result of memorisation by the memory unit 80 and of the computing module 61 by means of the specific parametric numbers PALi insofar as baseball pitching is concerned.

Figure 3:
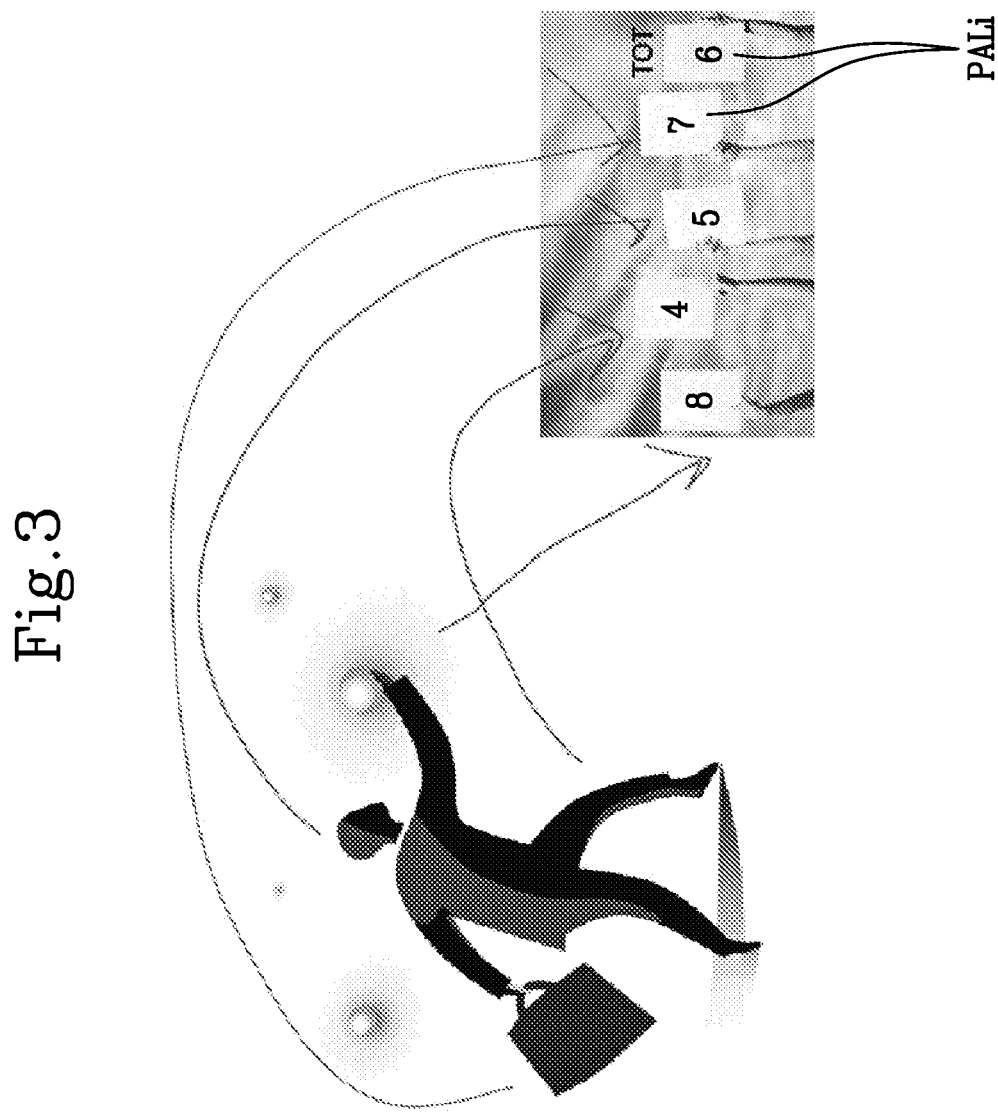

For each step identified, the ratio between the maximum values in degrees of rotation of the scapula at 20°, 40°, 60°, 80°, 100° and 120° degrees of abduction of the humerus had been previously computed, thus providing a total of 6 numbers in a barplot representation (FIG. 3).

The processing unit 60 further comprises a comparison module 62 configured to compare:
the computed parameters PALi and
predefined reference values $P_{REF}i$ representative of alteration thresholds $S_{AL}$ in said musculoskeletal system;

In other words, if the user had previously selected the reference data or remote data that had been loaded in the background, the barplot representations will automatically display secondary barplot representations in addition to the primary ones, with a different colour than before.

The processing unit 60 further comprises an identification module 63 configured to identify the alterations AL as a function of a failed matching between the computed parameters PALi and the predefined reference values $P_{REF}i$.

Comparative values, in particular of the ratios, are represented at the end as "clinical scores" and an overall score summarizing all the previous values (being an average of the ratio values) is presented to the user.

Each "clinical score" is computed as a function of the joint parameters Pz of one or more joints ATz affected by the movement or as a function of another clinical score.

The technical effect achieved is the weighting of a score deriving from one or more positive effects of a joint movement or muscle contraction compared to one or more negative effects of a joint movement or muscle contraction (for example, compensatory effects), whilst at the same time increasing the accuracy and robustness in identifying the alteration.

The invention comprises a classification module 64 for determining the belonging of an alteration to one or more groups of musculoskeletal pathologies of the upper limbs, as a function of the identified alterations AL and, in particular, also of the movement steps Fkz they correspond to.

For this purpose the invention comprises a display unit 70 configured to display the identified alterations AL.

For each identified step, the same screen displays secondary barplot information regarding quantities computed on the basis of EMG signals.

A specific control pushbutton is provided on the screen for printing out all the report details in a specific PDF file.

In a second preferred embodiment of the invention, the invention is applied to a scenario of a surgical intervention on a patient, where a surgeon operates on an injured knee of the patient using an open invasive procedure to replace a joint with a prosthesis.

The patient, i.e. the subject 1, has associated with him detecting means Ri capable of detecting physical quantities Qi representative of his state St.

In particular, the detecting means Ri are associated with the subject 1 on the sternum and thigh and tibia adjacent to the injured knee.

Preferably, the detecting means Ri comprise platforms based on sensors R1, preferably time synchronised with one another through a Wi-Fi or Bluetooth connection.

Preferably, the platforms are applied to the body of the subject using dedicated pull-off straps or adhesive material for the skin so that they are rigidly fixable to the segments in order to detect the physical quantities Qi representative of a state St of the subject.

A detecting unit 10 is configured to detect the physical quantities Qi through the detecting means Ri.

The detecting unit 10 operates in real time and collects the information, i.e. the physical quantities Qi coming from the aforesaid detecting means Ri or similar ones, aligning them in time, and sends this information to a low-level graphic user interface, in particular an identifying unit 20.

The identifying unit 20 is configured to identify a biomechanical model MBi for the subject 1.

The invention comprises a user instruction procedure that guides the user in all steps of the method of the invention.

In other words, the invention comprises a specific "wizard" which helps the user to identify and make decisions concerning strategies, to make corrections, to communicate with the subject undergoing examination or with another operator and to generate digital reports.

The technical effect achieved is to make the process of the invention also easy for non-specialised personnel to understand and use.

The user instruction procedure comprises a graphic interface 21 configured to perform one or more among the steps of:
checking the detection of the physical quantities Qi;
changing the display method;
showing how to position the detecting means Ri;
showing how to activate the detecting means Ri;
showing operators how to position the subject 1 for a correct analysis;

The generation of the biomechanical model MBi of the subject 1 takes place as a function of the execution of one or more of the preceding steps.

The technical effect achieved is a generation of a virtual representation of clinical information for the user who is not expert with the applied measurement protocol, data processing algorithms and the applied technology.

In other words, the graphic interface 21 is provided with pushbuttons and controls that guide the user through a step-by-step procedure controlled by the identifying unit 20.

A first screen shows the procedure for activating the detecting means Ri, the connection with the detecting means Ri and the selection of the type of surgical operation/scenario, and the type of display requested.

The connection with the detecting means is activated automatically and maintained until the user decides to stop the analysis via a dedicated pushbutton.

In a second screen, it is explained to the user how to position the detection means Ri already connected on the body of the subject 1, followed by a wait for the user to continue the step-by-step procedure. Preferably, the instructions are provided in the form of a video integrated in the screen.

In the second screen, the identifying unit 20 asks the user to wait for a predefined time, for example 10 seconds, before proceeding to the next step in order to enable the detecting unit 10 to stabilise the sensor outputs.

The second screen also shows the movements allowed to the knee and to the user in this period. Preferably, the instructions are provided in the form of a video integrated in the screen.

In a third screen, the identifying unit 20 explains to the user how to position the subject 1 in a supine position, with his injured knee totally extended. The screen provides instructions on the number of seconds the subject must be maintained in this position. Subsequently, visual feedback is provided with the display method previously selected by the user in an environment of 3D representation of the femur and tibia as aligned during the supine positioning, providing visual feedback as to the quality of this alignment. The screen then waits for the user to go ahead with the step-by-step procedure.

In a fourth screen, the identifying unit 20 asks the user of to keep the thigh upright until reaching a certain knee flexion threshold.

When the threshold is reached, an audio signal is provided to the user. The user is invited to bend the knee manually within a limited range of movement. In this situation, the actual mechanical axis of rotation described by the knee is evaluated. Visual feedback is provided to the user if the calibration was successful; otherwise the user is asked to repeat the procedure.

If the procedure is successful, the identifying unit 20 shows, in a fifth screen, a biomechanical description BMi of the human body segments involved in the analysis with the identified detecting means.

The technical effect achieved is the maintenance of a constant ratio between the detecting means Ri and anatomical body segments such as the torso, thigh and tibia adjacent to the knee undergoing examination.

In other words, and summing up, identifying a biomechanical model MBi for the subject 1 comprises the steps of:
asking the user for specific measurements MISi in order to calibrate the system as a function of scenario, environment and number of detecting means Ri applied to the subject 1;
asking the user to carry out a specific procedure of anatomic positioning, based on the biomechanical description of human body segments and joints.

The technical effect achieved is a specific, optimised multi-segment and multi-joint analysis on the subject which ensures a limitation of the variability among subsequent analyses of the same subject or similar analyses of different subjects due to errors both in the biomechanical model and in hardware components. This improves the reliability of the data generated and in general of the system of the invention.

At the end of the analysis, the identifying unit 20 provides feedback to the user to confirm the correct conclusion of the generation of the biomechanical description of the human body segments involved in the analysis. If this generation is not successfully concluded, the identifying unit 20 invites the user to repeat the previous steps again.

The 3D environment provides a real-time visual representation of the femur and tibia which reflect the current orientation in space of the subject's thigh and leg.

The determining unit 30 is configured to determine combined movements MCij of muscles Mi and bones Oj as a function of the physical quantities Qi detected and of the identified biomechanical model MBi.

Muscles Mi and bones Oj are shown respectively in FIGS. 2a and 2b.

In a fourth screen, the determining unit 30 uses the biomechanical model MBi of the preceding step and combines it with a method for extracting joint rotation angles in order to compute the joint kinematics in real time for each data sample. Joint angles include 3D knee flexion-extension rotation angles, knee abduction-adduction and internal-external knee rotation.

A display module 31 of the determining unit 30 is configured to display the muscles Mi and bones Oj in a combined view, preferably three-dimensional.

For each data sample, the values in degrees are transferred to the display method previously selected by the user in order to monitor the virtual joints in the 3D environment.

A specific part of the determining unit 30 controls the way in which these values are converted so as to generate the 3D movement, that is, the combined movement MCij.

With reference to FIG. 2b, the combined movement 3D is displayed in the form of a human skeleton, including the femur and tibia of the limb operated on, represented by bones in a virtual 3D environment.

The invention comprises a conversion unit 40 (FIG. 1) configured to convert said combined movements MCij into a plurality of movement steps Fkz of segments SEk and joints ATz.

In other words, the conversion unit 40 carries out a segmentation of the previously recorded process, identifying the steps of the movement.

The identified movement steps are displayed in a second part of the fifth screen, which comprises dedicated panels showing a Cartesian plane XY that is updated point by point using the angular values computed for each data sample.

Since the subject of examination is a knee, the X axis represents the time (in seconds) and the Y axis shows the angle of extension-flexion of the knee (values in degrees).

Similar graphic representations are provided for abduction-adduction of the knee and internal-external rotation of the knee.

By means of a specific control pushbutton the user can choose whether or not to render a specific background of the Cartesian plane visible in such a way as to show previously recorded values of the same type used for the real-time display.

In other words, the screen maintained active for the user during the surgical operation enables a real-time 3D verification of the rotations of the knee compared to the reference, both in a supine position and during passive knee flexion or extension, in order to correctly insert a knee spacer and connect the femur to the tibia or identify any excesses that could obstruct movement.

When the user presses the stop pushbutton, i.e. interrupts the simulation, a memory unit 80 (FIG. 1) memorises the virtual 3D movement and the graphic session in a file, preferably proprietary.

The invention comprises a processing unit 60 for processing alteration data.

The processing unit 60 comprises a computing module 61 configured to compute parameters PALi representative of the alterations AL as a function of either or both:
  the movement steps Fkz;
  the biomechanical model (MBi);

The technical effect achieved is the real-time obtainment of numbers that are easy to interpret, memorise, compare and share, both during the operation in order to introduce modifications to the alignment of the limbs to the joint and subsequently, for the purpose of documentation.

In other words, a sixth screen displays the memorisation result of the memory unit 80 and of the computing module 61 by means of the specific parametric numbers PALi regarding the range of possible movement obtained after a repositioning of the knee in passive movements.

The processing unit 60 further comprises a comparison module 62 configured to compare:
  the computed parameters PALi and
  predefined reference values $P_{REF}i$ representative of alteration thresholds $S_{AL}$ in said musculoskeletal system;

In other words, if the user had previously selected the reference data or remote data that had been loaded in the background, the system will automatically display secondary barplot representations in addition to the primary ones, with a different colour than before.

The processing unit 60 further comprises an identification module 63 configured to identify said alterations AL as a function of a failed matching between said computed parameters PALi and said predefined reference values $P_{REF}i$.

Values of the ratios are represented, finally, as "clinical scores" and an overall score summarizing all the previous values (being an average of the ratio values) is presented to the user.

Each "clinical score" is computed as a function of the joint parameters (Pz) or as a function of another clinical score.

The technical effect achieved is the weighting of a score deriving from one or more positive effects of a knee joint movement or muscle contraction compared to one or more negative effects of a knee joint movement or muscle contraction (for example, compensatory effects), while simultaneously increasing the accuracy and robustness in identifying the alteration.

For this purpose the invention comprises a display unit 70 configured to display the identified alterations AL.

A specific control pushbutton is available on the screen for printing out all the details of the report in a specific file, for example in PDF format.

The present invention in general achieves the following technical effects:
  efficient detection of alterations in the musculoskeletal system of a specific subject;
  precision in identifying the alteration;
  ease of understanding and use also for non-specialised personnel.

The processing unit 60 and in general the other computing units in the present description and in the subsequent claims may be presented as divided into distinct functional modules (memory modules or operating modules) for the sole purpose of describing their functions in a clear and complete manner.

In reality, the units can consist of a single electronic device, suitably programmed to perform the functions described, and the various modules can correspond to hardware entities and/or routine software belonging to the programmed device.

Alternatively, or in addition, such functions may be performed by a plurality of electronic devices over which the aforesaid functional modules can be distributed.

The units can further rely on one or more processors for the execution of the instructions contained in the memory modules.

The units and the aforesaid functional modules can moreover be distributed over different local or remote computers based on the architecture of the network they reside in.

The invention claimed is:

1. A method for identifying at least one alteration in a musculoskeletal system of a subject, the method comprising:
  associating, with said subject, detecting means comprising sensors for electrical activity detection configured to detect physical quantities representative of a state of said subject, wherein said associating comprises positioning said detecting means on said subject;
  detecting, in real time, said physical quantities through said detecting means, aligning said physical quantities in time, and sending said physical quantities to an identifying unit, wherein said identifying unit controls a step-by-step user instruction procedure that guides a user by means of a graphic interface provided with buttons and controls, the guiding of the user by means of the graphic interface comprising showing the user how to position said detecting means on the subject and how to activate the detecting means;

generating a biomechanical model for said subject by said identifying unit, wherein the generating generates the biomechanical model as a function of execution of said step-by-step user instruction procedure, which provides an optimized multi-segment and multi joint analysis on the subject;

providing, by the identifying unit, a feedback to the user confirming successful conclusion of the generating of the biomechanical model for said subject;

determining combined movements of muscles and bones as a function of said physical quantities and said biomechanical model, and displaying the muscles and the combined movements of muscles and bones on a display, the muscles being represented by textures with colors of the textures being dynamically controlled to modulate the colors based upon values of signals received from the detecting means and a set of threshold values;

converting said combined movements of muscles and bones into a plurality of movement steps of human body segments of the subject and human body joints of the subject, wherein said movement steps are computed as a function of:

first joint parameters (Pz) of a first joint (Atz) and at least one second joint parameter (Pz+1) computed as a function of second joints (Az+1) affected by the movement of the first joint (Atz);

identifying the at least one alteration based on a failed matching between parameters (PALi), determined based on the plurality of movement steps, and predefined reference values representative of alteration thresholds in the musculoskeletal system, wherein the identifying is carried out by an identification module of said processing unit; and determining a belonging of said at least one alteration to one or more groups of musculoskeletal pathologies, wherein the determining is carried out by a classification module of said processing unit.

2. The method of claim 1, wherein said graphic interface is configured to perform one or more among:
controlling the detection of the physical quantities;
changing a display method; and
showing the subject positioning for a correct analysis.

3. The method of claim 1, further comprising displaying said at least one alteration in real time.

4. The method of claim 3, further comprising utilizing the biomechanical model with a method for extracting joint rotation angles in order to compute joint kinematics in real time, wherein the joint rotation angles include 3D rotation angles of humerothoracic, glenohumeral and scapulothoracic joints.

5. The method of claim 1, wherein said determining said combined movements of said muscles and said bones comprises displaying said muscles and said bones in a combined view, the combined view including a three-dimensional representation.

6. The method of claim 1, wherein said generating said biomechanical model for said subject comprises:
asking the user for specific measurements in order to calibrate a system for identifying the at least one alteration as a function of:
scenario;
environment; and
number of detecting means applied to the subject; and
asking the user to carry out a specific procedure of positioning anatomy of the subject based on a biomechanical description of the human body segments and the human body joints, by means of a validated measuring protocol.

7. The method of claim 1, wherein said first joint parameters and said at least one second joint parameter are numerical parameters.

8. A system for identifying at least one alteration in a musculoskeletal system of a subject, wherein the system comprises:
detecting means comprising sensors for electrical activity detection configured to be associated with said subject, the detecting means being capable of detecting physical quantities representative of a state of said subject, wherein said detecting means are configured to be positioned on said subject;

a detecting unit configured to detect, in real time, said physical quantities through said detecting means, align said physical quantities in time, and send said physical quantities to an identifying unit, wherein said identifying unit is configured to control a step-by-step user instruction procedure that guides a user by means of a graphic interface provided with buttons and controls, the guiding of the user by means of the graphic interface comprising showing the user how to position said detecting means on the subject and how to activate the detecting means;

the identifying unit being configured to generate a biomechanical model for said subject, wherein the biomechanical model is generated as a function of execution of said step-by-step user instruction procedure, which provides an optimized multi-segment and multi joint analysis on the subject;

wherein said identifying unit is further configured to provide a feedback to the user confirming successful conclusion of the generating of the biomechanical model for said subject;

a determining unit configured to determine combined movements of muscles and bones based upon said physical quantities and said biomechanical model, and to display the muscles and the combined movements of muscles and bones on a display, the muscles being represented by textures with colors of the textures being dynamically controlled to modulate the colors based upon values of signals received from the detecting means and set of threshold values;

a conversion unit configured to convert said combined movements into a plurality of movement steps of human body segments of the subject and human body joints of the subject, wherein said movement steps (Fkz) are computed as a function of:
first joint parameters (Pz) of a first joint (ATz); and
at least a second joint parameter (Pz+1) computed as a function of second joints (ATz+1) affected by the movement of the first joint (ATz);

an identification module configured to identify the at least one alteration based on a failed matching between parameters (PALi), determined based on the plurality of movement steps, and predefined reference values representative of alteration thresholds in the musculoskeletal system; and a classification module configured to determine an association of said at least one alteration to one or more groups of musculoskeletal pathologies.

9. The system of claim 8, wherein said graphic interface is configured to perform one or more among:
controlling the detection of the physical quantities ($Q_i$);
changing a display method; and
showing the subject positioning for a correct analysis.

10. The system of claim 8, further comprising a unit configured to display said at least one alteration.

11. The system of claim 10, wherein the determining unit is configured to use the biomechanical model with a method for extracting joint rotation angles in order to compute joint kinematics in real time, wherein the joint rotation angles include 3D rotation angles of humerothoracic, glenohumeral and scapulothoracic joints.

12. The system of claim 8, wherein said determining unit comprises a module configured to display said muscles and said bones in a combined view, the combined view including a three-dimensional view.

13. The system of claim 8, further comprising a memory unit for storing indications of said combined movements and a combined view of said muscles and said bones.

14. The system of claim 8, wherein said identifying unit further comprises:
a first request module configured to ask the user for specific measurements in order to calibrate the system as a function of:
scenario;
environment;
number of detecting means applied to the subject; and
a second request module configured to ask the user to carry out a specific procedure of positioning anatomy of the subject as a function of a biomechanical description of the human body segments and the human body joints.

* * * * *